United States Patent
Kleine et al.

(10) Patent No.: US 11,116,215 B2
(45) Date of Patent: Sep. 14, 2021

(54) AQUEOUS ANTIMICROBIAL FILM-FORMING COMPOSITION FOR TEAT TREATMENT BY SPRAY APPLICATION

(71) Applicant: ECOLAB USA INC., Saint Paul, MN (US)

(72) Inventors: Tillmann Kleine, Cologne (DE); Jonathan Scott Killeen, Mannheim (DE); Helen Breiderhoff, Nettetal (DE); Michael Schneider, Grevenbroich (DE)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 15/739,087

(22) PCT Filed: Jun. 23, 2015

(86) PCT No.: PCT/EP2015/064166
§ 371 (c)(1),
(2) Date: Dec. 21, 2017

(87) PCT Pub. No.: WO2016/206729
PCT Pub. Date: Dec. 29, 2016

(65) Prior Publication Data
US 2018/0177189 A1   Jun. 28, 2018

(51) Int. Cl.
| | | |
|---|---|---|
| A01N 43/36 | (2006.01) |
| A61K 9/00 | (2006.01) |
| A61K 33/18 | (2006.01) |
| A01N 59/12 | (2006.01) |
| A61K 47/32 | (2006.01) |
| A61K 47/34 | (2017.01) |
| A61K 9/70 | (2006.01) |
| A01N 25/10 | (2006.01) |
| A01N 25/30 | (2006.01) |

(52) U.S. Cl.
CPC ............. *A01N 43/36* (2013.01); *A01N 25/10* (2013.01); *A01N 25/30* (2013.01); *A01N 59/12* (2013.01); *A61K 9/0014* (2013.01); *A61K 9/7015* (2013.01); *A61K 33/18* (2013.01); *A61K 47/32* (2013.01); *A61K 47/34* (2013.01)

(58) Field of Classification Search
CPC ........ A01N 25/10; A01N 59/12; A01N 25/22; A01N 25/24; A01N 25/30; A01N 43/36; A61K 33/18; A61K 47/32; A61K 47/34; A61K 9/0014; A61K 9/7015
See application file for complete search history.

(56) References Cited

U.S. PATENT DOCUMENTS

| | | | |
|---|---|---|---|
| 4,271,149 A | 6/1981 | Winicov et al. | |
| 5,017,369 A | 5/1991 | Marhevka | |
| 5,154,920 A * | 10/1992 | Flesher | A01N 25/24 106/15.05 |
| 5,310,549 A | 5/1994 | Bull | |
| 5,368,868 A | 11/1994 | Winicov | |
| 5,503,838 A | 4/1996 | Schmidt et al. | |
| 5,618,841 A | 4/1997 | Kross | |
| 6,042,818 A * | 3/2000 | Bragulla | A01N 47/44 424/405 |
| 6,294,186 B1 * | 9/2001 | Beerse | A01N 43/36 424/401 |
| 6,749,869 B1 | 6/2004 | Richter et al. | |
| 7,547,421 B2 | 6/2009 | McSherry et al. | |
| 8,017,082 B2 | 9/2011 | McSherry et al. | |
| 2001/0056127 A1 * | 12/2001 | Kessler | A61K 8/20 514/772.4 |
| 2004/0115228 A1 | 6/2004 | Costa et al. | |
| 2005/0038280 A1 * | 2/2005 | Lai | C07C 329/00 558/235 |
| 2011/0177145 A1 * | 7/2011 | Erkenbrecher, Jr. | A01N 37/16 424/405 |

FOREIGN PATENT DOCUMENTS

| | | |
|---|---|---|
| CN | 101439044 A | 5/2009 |
| CN | 102595808 A | 7/2012 |
| JP | 200041529 A | 2/2000 |
| JP | 2010503531 A | 2/2010 |
| JP | 2011500790 A | 1/2011 |
| JP | 2013500344 A | 1/2013 |

(Continued)

OTHER PUBLICATIONS

European Patent Office, "International Search Report and Written Opinion of the International Searching Authority," in connection to PCT/EP2015/064166, filed Jun. 23, 2015, dated Jul. 21, 2015.
The Dow Chemical Company, "It's time to Rethink rheology", PDF, www.dowcoatingmaterials.com, 17 pages, 2012.
BASF SE, "BASF's Rheology Modifiers: Selection Guide", PDF, www.basf.com/solution-finder, 2 pages, 2017.
BASF, "Formulation challenges and product recommendations", https://www.dispersions-pigments.basf.com/portal/load/fid806725/Rheology%20Modifiers%20Product%Recommendations%20for%20Asia%20Pacific.pdf, Published Jun. 13, 2013, retrieved from the Internet on Oct. 16, 2019.

(Continued)

Primary Examiner — Michael B. Pallay
(74) Attorney, Agent, or Firm — McKee, Voorhees & Sease, PLC

(57) ABSTRACT

The present invention is directed to a sprayable aqueous antimicrobial film-forming composition comprising in an aqueous base:
(a) a film-forming polymer;
(b) an antimicrobial agent;
(c) a hydrophobically-modified ethoxylated urethane as rheology modifier;
(d) optionally, an anti-foaming agent.
Further, the present invention refers to the use of the composition for controlling mastitis in milk producing animals and a method for controlling mastitis in milk producing animals comprising applying by spraying the composition to a teat.

10 Claims, No Drawings

(56) References Cited

FOREIGN PATENT DOCUMENTS

WO       09804136 A1     2/1998
WO    2009118714 A2   10/2009

OTHER PUBLICATIONS

Kuraray et al., "Kuraray Poval™ and Elvanol™", https://www.kuraray.us.com/products/polymers/kuraray-poval-elvanol/, published on Oct. 14, 2014 as per Google search with the results restricted for before Jun. 23, 2015, 2 pages, Feb. 17, 2020.
Karsa et al., "Surfactants Applications Directory", p. 107 of Springer, ISBN 9789401053518, Chapter 10, pp. 71-121, 2012.

* cited by examiner

AQUEOUS ANTIMICROBIAL FILM-FORMING COMPOSITION FOR TEAT TREATMENT BY SPRAY APPLICATION

CROSS REFERENCE TO RELATED APPLICATION

This is a U.S. National Phase application claiming priority to PCT/EP2015/064166 filed Jun. 23, 2015, the entire contents of which are hereby expressly incorporated by reference in its entirety, including, without limitation, the specification, claims, and abstract, as well as any figures, tables or drawings thereof.

The present invention is directed to a sprayable aqueous antimicrobial film-forming composition. In particular, the invention provides compositions and formulations for the control of mastitis in milk producing animals.

BACKGROUND

Field of the Invention

The present invention is directed to the field of topical antimicrobial liquid compositions of the type that may be used to control or destroy pathogenic microorganisms. Antimicrobial compositions may be used to reduce the risk of infection and include the control of pathogenic organisms on skin surfaces, in particular for the control or prevention of mastitis. Prevention of mastitis is a major goal of the dairy industry. Contact of the bovine or ovine mammary gland with pathogenic microorganisms, usually bacteria but occasionally yeast or fungi, can result in the disease of mastitis.

Milking of cows on a large scale is almost entirely done with a milking machine. The milking machine draws the milk from the cow's udder by pulsating vacuum, e.g., by attaching a teat cup connected to a vacuum pump and pulsating the vacuum to alternately allow the milk to fill and drain from the area of the udder and teat to simulate hand milking of the cow. The tendency is to minimize the milking time by using high vacuum which can cause irritation or damage to the teat and udder.

The damage to tissue caused by the milking machine followed by exposure of the damaged tissue to certain microorganisms can result in an infection known as mastitis. Control of mastitis is of great economic importance to dairy farmers because an infected cow's contaminated milk cannot be marketed. The udder and teats of an infected cow can be treated with an antibiotic to inhibit the spread of mastitis causing pathogens. However, the milk from such cows cannot be sold until the antibiotic is absent from the milk, which usually is about 3-5 days after the last treatment.

To reduce mastitis, commercial teat dips have been developed which are usually administered to the teat by dipping or spraying the teat prior to milking as well as after removal of the milking cup. Teat dips applied subsequent to milking may form a thick composition, film or barrier that remains on the teat until the next milking, which is generally 8 to 12 hours later. According to experts, prevention of mastitis by the dipping of teats in an antimicrobial (biostatic or biocidal) solution is one of the most effective procedures that a dairy farmer can follow.

An essential function of a teat dip is to prevent mastitis by killing or controlling infectious microorganisms. The teat dip product desirably has a wide spectrum of antibacterial activity (i.e., it can kill or inhibit the growth of a wide variety of mastitis-causing microorganisms), and has emollient properties to prevent irritation of the skin on which it is applied.

A number of teat dip products or mastitis control agents are available to dairy farmers which have varying degrees of effectiveness. These products or agents have in common an antimicrobial agent which is an active ingredient (usually the principal active ingredient) of the treating solution. Commercially available teat dips may be divided into two primary classifications, namely, non-barrier and barrier dips. The non-barrier teat dips are strictly antimicrobial and are applied to kill microorganisms that are already present in the teat canal or on the surface of the teat skin. By design, the microbiological effect is substantially immediate, targeting the contagious organisms that may be transferred between animals during the pre-milking, milking and post milking process. The barrier dips may also be antimicrobial and are applied to form a prophylactic film or coating that may prevent microbes from contacting the teat.

Teat dips have used a variety of antimicrobial agents including iodophors, PVP-iodine (a particular iodophor), hypochlorites, chlorine dioxide, chlorinated isocyanurates (chlorinated-S-triazene-trione), bromine, hydroxyquinone, ammonium chloride, chlorhexidine, hexachlorophene, diaphene, cetyl pyridinium chloride, and the quaternary ammonium germicides. Of the topically applied antimicrobial agents (i.e., those agents applied directly to the skin) which have been investigated for control of bovine mastitis, iodophors, quaternary ammonium compounds, and chlorine-releasing agents (particularly sodium hypochlorite and, more recently, chlorinated isocyanurates) appear to have gained the widest acceptance among dairy farmers, despite the fact that some of the chlorine-releasing sanitizers (e.g. 4% aqueous NaOCl) can have an irritating effect upon cow teats.

In the control of bovine mastitis, rapid killing of bacteria is essential, since prolonged treatment (e.g. more than 15 minutes or even more than a minute) with the teat dip is normally impractical. Bactericidal tests of teat dip formulas are most informative when they are conducted with a view toward measuring their short-term kill.

The document WO 98/04136 discloses a teat dip composition for protecting against infections containing a film-building element and one or more several active disinfectant substances. The film-building agent comprises as film-building agent polyvinyl alcohol polymers or copolymers, as active disinfectant substance iodine in the form of polyvinylpyrrolidone iodine and/or chlorhexidine; and ether carboxylic acids. The composition is particularly suitable to protect the teats and udders of cows, ewes and goats after milking and forms a visible, mechanically resistant film.

Object of the Present Invention

Some of the available teat dip agents suffer from serious drawbacks. The film-forming teat dips of the prior art are not suitable to be sprayed onto the skin. Further, when using existing film-forming compositions for spray application nozzle failure occurs, which makes such compositions of the state of art useless for spray application. Existing spray products having a microbiological effect are not generating a protecting barrier after treatment. When carrying out the studies for providing antimicrobial film-forming compositions for spray application the inventors found that when using currently available barrier products for spraying excessive foam formation is negatively influencing the barrier properties and therefore leading to insufficient protection of the teat and the mammary ducts. Using a defoamer in order to prevent foam formation on the teat the spray properties significantly improved, however, the wetting and sticking properties on skin were negatively influenced. Due to the growing herd sizes and a continuous automation of the milking process the demand for a barrier product for spray application is growing. Therefore, the object of the present invention was to provide an antimicrobial film-forming composition having good spray properties and which do not cause nozzle failure, which composition has good wetting and sticking properties on skin and which disinfecting and anti-microbial properties is comparable to existing products, i.e. which composition is suitable for use as sprayable composition to protect against or to reduce the incidence of mastitis.

SUMMARY OF THE INVENTION

The technical object of the present invention is solved by a sprayable aqueous antimicrobial film-forming composition comprising in an aqueous base:
  (a) a film-forming polymer;
  (b) an antimicrobial agent;
  (c) a hydrophobically-modified ethoxylated urethane as rheology modifier;
  (d) optionally an anti-foaming agent.

In a preferred embodiment the sprayable aqueous antimicrobial film-forming composition according to the present invention comprises in an aqueous base:
  (a) 0.1 to 10.0 wt.-% of a film-forming polymer;
  (b) 0.1 to 10.0 wt.-% of an antimicrobial agent;
  (c) 0.001 to 3.0 wt.-% of a hydrophobically-modified ethoxylated urethane as rheology modifier;
  (d) optionally 0.001 to 3.0 wt.-% of an anti-foaming agent.

In a further preferred embodiment the sprayable aqueous antimicrobial film-forming composition according to the present invention comprises in an aqueous base:
  (a) 1.0 to 5.0 wt.-% of a film-forming polymer;
  (b) 0.5 to 7.0 wt.-% of an antimicrobial agent;
  (c) 0.01 to 1.0 wt.-% of a hydrophobically-modified ethoxylated urethane;
  (d) optionally 0.005 to 1.0 wt.-% of anti-foaming agent;
  more preferred:
  (a) 2.0 to 4.5 wt.-% of a film-forming polymer;
  (b) 0.5 to 5.0 wt.-% of an antimicrobial agent;
  (c) 0.05 to 0.5 wt.-% of a hydrophobically-modified ethoxylated urethane;
  (d) optionally 0.02 to 0.2 wt.-% of anti-foaming agent.

In further preferred embodiments the sprayable aqueous antimicrobial film-forming composition according to the present invention comprises in an aqueous base:
  (a) 0.1 to 10.0 wt.-% of polyvinyl alcohol as film-forming polymer;
  (b) 0.1 to 10.0 wt.-% of an antimicrobial agent;
  (c) 0.001 to 3.0 wt.-% of a hydrophobically-modified ethoxylated urethane as rheology modifier;
  (d) optionally 0.001 to 3.0 wt.-% of an anti-foaming agent.
  more preferably:
  (a) 1.0 to 5.0 wt.-% of polyvinyl alcohol as film-forming polymer;
  (b) 0.5 to 7.0 wt.-% of an antimicrobial agent;
  (c) 0.01 to 1.0 wt.-% of a hydrophobically-modified ethoxylated urethane;
  (d) optionally 0.005 to 1.0 wt.-% of anti-foaming agent;
  still further preferred:
  (a) 2.0 to 4.5 wt.-% of polyvinyl alcohol as film-forming polymer;
  (b) 0.5 to 5.0 wt.-% of an antimicrobial agent;
  (c) 0.05 to 0.5 wt.-% of a hydrophobically-modified ethoxylated urethane;
  (d) optionally 0.02 to 0.2 wt.-% of anti-foaming agent.

The sprayable aqueous antimicrobial film-forming composition according to the present invention is formulated and suitable to reduce the incidence of both contagious mastitis and environmental mastitis in a dairy herd.

The present inventors have found the formulation of an aqueous composition comprising an antimicrobial agent, in particular an effective mastitis preventing or treating agent, a film-forming polymer, preferably polyvinyl alcohol, a rheology modifier or thickener in the form of a hydrophobically-modified ethoxylated urethane and optionally in addition an anti-foaming agent, provides a teat treatment composition that can be sprayed and exhibits film-forming properties, antimicrobial properties against the typical contagious mastitis causing pathogens and barrier properties protecting the animal from environmental mastitis. The material can be formulated such that a film is formed that can be easily removed prior to milking. The aqueous material of the invention can be used in treating dairy herds. After milking, the material is applied to the skin of the udder and teats by spray application to form the antimicrobial barrier coating to prevent or reduce contagious mastitis. The animal is then released into the environment where the material can protect the animal from contamination from the environment but will be resistant to environmental water such as rain, ponds, mud, etc. remaining on the animal for the period between milkings. When the animal returns to the milking site, the antimicrobial barrier coating can be easily removed in a few minutes using an aqueous wash. Milking can continue without delay and after milking is finished, the animal can again be treated with the aqueous material forming a new antimicrobial barrier film.

In particular, the aqueous antimicrobial film-forming composition of the present invention is suitable to be sprayed onto the skin of teats and udder and generates a protecting barrier after treatment. Moreover, the composition does not cause nozzle failure even when it remains in the spray gun and nozzle for prolonged time periods.

The present inventors surprisingly found that when using a hydrophobically-modified ethoxylated urethane as rheology modifier a film-forming composition can be provided that has good spray properties, good wetting and sticking properties on skin and which after spray application produces a film having good barrier properties as well.

In addition, the present inventors surprisingly found that the combination of an anti-foaming agent and hydrophobically-modified ethoxylated urethane as rheology modifier provides a film-forming composition that has even better spray properties, wetting and sticking properties on skin and which after spray application produces a film having good barrier properties as well.

Further, the composition of the present invention is sprayable within a temperature range from 0° C. to 40° C. and preferably at least within a temperature range from 5° C. to 30° C.

As mentioned above, in the composition of the present invention hydrophobically-modified ethoxylated urethane is used which is a polymer having polyethylene glycol building blocks and urethane building blocks, wherein the polymer chain is end-capped with hydrophobic groups.

In a preferred embodiment of the present invention the antimicrobial agent is selected from the group consisting of $I_2$, an iodophor, in particular in the form of polyvinyl pyrrolidone iodine (PVP-iodine), linear or branched chain aliphatic $C_4$-$C_{10}$ carboxylic acid, in particular capric and caprylic acids, octanoic acid, nonanoic acid, decanoic acid; lactic acid, salicylic acid, peroxycarboxylic acid, sulfoperoxycarboxylic acid, $C_1$-$C_4$ alkanols, isopropyl alcohol, benzyl alcohol, bronopol (2-bromo-2-nitro-1,3-propanediol), sodium pyridinathione, chlorohexidine, chlorhexidine diacetate, chlorhexidine digluconate, quaternary ammonium compounds such as the salts of alkyl dimethylbenzyl ammonium, dialkyl dimethyl ammonium compounds and benzethonium; sulfonic acids, hypohalous acid, alkali hypohalites, chlorine dioxide precursors, chlorine-releasing agents (particularly sodium hypochlorite and, more recently, chlorinated isocyanurates), hypochlorites, chlorine dioxide, chlorinated isocyanurates (chlorinated-S-triazene-trione), bromine, hydroxyquinone, ammonium chloride, hexachlorophene, diaphene, cetyl pyridinium chloride, acid anionics (e.g. alkylaryl sulfonic acids, aryl sulfonic acid, alkyl sulfonic acids, alkylaryl sulfuric acid, aryl sulfuric acid, alkyl sulfuric acid, alkylaryl sulfuric acid), phenolic antimicrobial agents may be chosen from ortho-phenyl phenol, 2,4,4'-trichloro-2"-hydroxydiphenylether, 4-chloro-3,5-dimethyl phenol, polyhexamethyl biguanide (CAS 32289-58-0), guanidine salts such as polyhexamethylene guanidine hydrochloride (CAS 57028-96-3), polyhexamethylene guanidine hydrophosphate (CAS 89697-78-9), and poly[2-(2-ethoxy)-ethoxyethyl]-guanidinium chloride (CAS 374572-91-5) and mixtures thereof. Typically the composition of the present invention comprises more than one type of antimicrobial agents.

In a further preferred embodiment of the present invention as antimicrobial agent an iodophor in the form of polyvinyl pyrrolidone iodine (PVP-iodine) is comprised. However, in other preferred embodiments in addition to polyvinyl pyrrolidone iodine further antimicrobial agents can be comprised.

Further preferred, the composition of the present invention further comprises alkylbenzene sulfonic acid used as antimicrobial agent.

In further preferred embodiments the composition of the present invention is further comprising polyoxypropylene alkylether carboxylic acid, in particular having the following formula R—O—$(C_3H_6$—O$)_m$—$(O_2H_4$—O$)_n$—$CH_2$—COOH, wherein R is an alkyl group having 4 to 10 carbon atoms, m is an integer from 0 to 8 and n is an integer from 0 to 8, wherein at least one of m or n is not 0. Preferably, the inventive composition comprises polyoxyethylene alkylether carboxylic acid having the following formula R—O—$(C_2H_4$—O$)_n$—$CH_2$—COOH, wherein R is an alkyl group having 4 to 10 carbon atoms and n is an integer from 2 to 8.

In a further preferred embodiment of the sprayable aqueous antimicrobial film-forming composition polyvinyl alcohol and/or polysulfonic acid is present, preferably both polyvinyl alcohol and polysulfonic acid are present in the composition as film-former. In a particularly preferred embodiment polyvinyl alcohol and/or polysulfonic acid as well as polyvinyl pyrrolidone iodine is present, preferably both polyvinyl alcohol and polysulfonic acid as film former as well as polyvinyl pyrrolidone iodine as antimicrobial agent are present in the composition.

In a particularly preferred embodiment of the present invention, the sprayable aqueous antimicrobial film-forming composition comprises in an aqueous base:
(a) 0.1 to 10.0 wt.-% of polyvinyl alcohol as film-forming polymer;
(b) 0.5 to 10.0 wt.-% of polyvinyl pyrrolidone iodine as antimicrobial agent;
(c) 0.001 to 3.0 wt.-% of a hydrophobically-modified ethoxylated urethane as rheology modifier;
(d) 0.001 to 3.0 wt.-% of an anti-foaming agent.

In another particularly preferred embodiment of the present invention, the sprayable aqueous antimicrobial film-forming composition comprises in an aqueous base:
(a) 0.1 to 10.0 wt.-% of polyvinyl alcohol as film-forming polymer;
(b) 0.5 to 10.0 wt.-% of polyvinyl pyrrolidone iodine as antimicrobial agent;
(c) 0.001 to 3.0 wt.-% of a hydrophobically-modified ethoxylated urethane as rheology modifier;
(d) 0.001 to 3.0 wt.-% of an anti-foaming agent;
(e) 0.05 to 5.0 wt.-% of polysulfonic acid;
(f) 0.05 to 5.0 wt.-% polyoxyethylene alkylether carboxylic acid having the following formula R—O—$(C_2H_4$—O$)_n$—$CH_2$—COOH, wherein R is an alkyl group having 4 to 10 carbon atoms and n is an integer from 2 to 8;
(g) optionally, 0.01 to 5.0 wt.-% of a further antimicrobial agent, preferably selected from the group consisting of alkylbenzene sulfonic acid, chlorhexidine, orthophenyl phenol, lactic acid, carboxylic acid, in particular decanoic acid, and mixtures thereof, with the proviso that (b) is not more than 5.0 wt.-%.

In still another preferred embodiment the anti-foaming agent is a silicone-based anti-foaming agent.

In a particularly preferred embodiment of the present invention the sprayable aqueous antimicrobial film-forming composition has a Brookfield viscosity measured in cPs by a Brookfield LV viscosimeter at a temperature of 25° C. from 1 to 50 cPs, preferably from 1 to 20 cPs, more preferred from 1 to 5 cPs using a spindle #2 at 50 rpm.

The present invention also provides the use of the composition according to the present invention for controlling mastitis in milk producing animals.

Further, the present invention provides a method for controlling mastitis in milk producing animals comprising applying by spraying the composition of the present invention to a teat.

DETAILED DESCRIPTION OF THE INVENTION

Briefly, the novel sprayable aqueous antimicrobial film-forming composition comprises in an aqueous base:
(a) a film-forming polymer, preferably polyvinyl alcohol;
(b) an antimicrobial agent;
(c) a hydrophobically-modified ethoxylated urethane as rheology modifier;
(d) optionally, an anti-foaming agent,
and in particular is formulated and suitable to reduce the incidence of both contagious mastitis and environmental mastitis in a dairy herd.

The aqueous film-forming composition may contain other useful materials in the formulation to enhance the properties of the materials or to add new properties required by the dairy operator. The aqueous composition can be used to form a barrier film having antimicrobial properties on mastitis susceptible skin surface of a dairy animal. The barrier is long lived and flexible, provides barrier properties and is antimicrobial but can be rapidly removed prior to milking using an aqueous wash in typical dairy operations. The material may be applied to the dairy animal in a variety of ways: the material can be sprayed, brushed, dabbed, or flooded onto the susceptible site. The most preferred application mode is spray application. The material dries quickly to form a barrier layer. The barrier layer is flexible and resists cracking. The layer contains the antimicrobial material that kills microorganisms on the skin surface. Such antimicrobial action is important because the milking operation can often spread mastitis causing microorganisms which can under certain circumstances cause inflammation and infection in abraded or affected skin resulting from contact with milking machines during milking operations.

The terms "teat dip" or "teat dipping" shall be interpreted broadly and in accordance with the terminology used in the art of dairy farming. The composition is topically applied, however, it is not only intended for dipping of the teats but it can, of course, be applied in other ways, such as by spraying, which is particularly preferred, and still fall within the recognized terms teat dip or teat dipping composition or agent. The composition of the present invention is characterized in that it is suitable for spray application.

As used herein unless otherwise specified, the term "antimicrobial" describes a biocidal effect that may be, for example, an antibacterial, antifungal, antiviral, bacteriostatic, disinfecting, or sanitizing effect.

"Killing" as the term is used herein is meant to include actual killing as well as inhibition or abatement of microorganism growth.

The term "topical" shall refer to any composition which may be applied to the epidermis or other animal portion on which compositions might be applied.

The term "additive" shall mean any component that is not an antimicrobial agent or a pharmaceutical carrier. A pharmaceutical carrier is generally a bulk solvent used to dilute or solubilize the components of the composition, e.g., water.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

As used in this specification and the appended claims, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Weight percent, percent by weight, % by weight, wt.-%, and the like are synonyms that refer to the concentration of a substance as the weight of that substance divided by the weight of the composition and multiplied by 100.

Unless otherwise stated, all weight percentages provided herein reflect the active weight percent of each component. The weight percent of raw material as provided by the manufacturer is easily determined from the provided information by use of product data sheets as provided from the manufacturer.

The composition may further include one or more additives selected from a buffering agent, an emollient, a humectant, a preservative, a surfactant or wetting agent, a foaming agent, a colorant, an opacifying agent, a skin conditioning agent and any combinations thereof.

Film-Forming Polymer

Barrier and film-forming agents are those components of a teat dipping composition that remain in contact with the teat between milking cycles. Barrier and film-forming agents coat the teat skin and, optionally, the udder. Barrier agents may form a plug at the end of the open teat canal. Typical barrier and film-forming agents used according to the present invention include thick creams or emollients (made with viscosity control agents), films, polymers, latex and the like. Some nonionic surfactants may help further enhance the barrier properties of a composition, in addition to contributing to surface wetting. Examples of such surfactants may include, without limitation, polyoxyethylene-polyoxypropylene glycol (marketed as Pluronic® F108). Preferred barrier forming agents include, for example, latex, arabinoxylanes, glucomannanes, guar gum, johannistree gums, cellulose, methyl cellulose, ethyl cellulose, hydroxyethyl cellulose, hydroxymethyl cellulose, carboxyethyl cellulose, carboxymethyl cellulose, starch, hydroxyethyl starch, gum arabic, curdlan, pullulan, dextran, polysulfonic acid, polyacryl amide, high molecular weight polyacrylate, high molecular weight cross-linked polyacrylate, polyacrylic acid (carbomer), sodium alginate, sodium alginate cross-linked with calcium salt, xanthan gum, poly(vinyl alcohol) (PVA) and poly(N-vinylpyrrolidone) (PVP). A suitable example for a polysulfonic acid is polyacrylamidomethylpropane sulfonic acid commercially available as Rheocare™ HSP-1180.

In a particularly preferred embodiment of the present invention, in the sprayable aqueous antimicrobial film-forming composition polyvinyl alcohol is used as film-forming polymer and optionally further agents having film-forming properties are used in the composition, preferably polysulfonic acid and/or polyvinylpyrrolidone, wherein polyvinylpyrrolidone may be used for complexing iodine and as such then may be comprised in the composition as antimicrobial agent, namely polyvinyl pyrrolidone-iodine.

Polyvinyl alcohol (PVOH), a polyhydroxide polymer having a polymethylene backbone with pendent hydroxy groups, is a water soluble synthetic resin. The resin is produced by the hydrolysis of polyvinyl acetate. Polyvinyl alcohol is one of a limited number in the class of water soluble polymer materials. The resin is commonly available as a dry solid and is available in granular or powder form. The grades of polyvinyl alcohol include a partially hydrolyzed version having a degree of hydrolysis (the percentage of acetate groups removed from the polyvinyl alcohol leaving free hydroxyl groups) from about 87 to about 91%. An intermediate grade of hydrolysis in the polyvinyl alcohol produces a polymer having from about 91 to about 98% removal of acetate groups. A fully hydrolyzed grade of polyvinyl alcohol has from about 98 to about 99.5% of acetate groups removed. A polyvinyl alcohol product called superhydrolyzed PVOH has greater than 99.5% of the acetate groups removed.

Polyvinyl alcohol is commonly produced in nominal number average molecular weights that range from about 4,000 to about 100,000. Commonly, the molecular weight of commercial polyvinyl alcohol grades is reflected in the viscosity of a 4 wt.-% solution measured in centipoise (cP) at 20° C. (Hoeppler falling ball method). Variation of film flexibility, water sensitivity, ease of solvation, viscosity, film strength, adhesion, dispersing power can only be varied by adjusting molecular weight or degree of hydrolysis. Solutions of polyvinyl alcohol and water can be made with large quantities of lower alcohol cosolvents and salt cosolutes and with a number of other small molecular or polymeric additives or active constituents. Polyvinyl alcohol is made by first forming polyvinyl acetate or a vinyl acetate containing copolymer such as an ethylene vinyl acetate copolymer, and removing acetate groups by base hydrolysis. A production of polyvinyl acetate or vinyl acetate containing copolymer can be done using conventional polymerization processes which controls ultimate molecular weight. Catalyst selection, temperature, solvent selection, and chain transformation can be adjusted by persons skilled in polymerization arts to control molecular weight and other polymer structural attributes. The degree of hydrolysis is controlled by preventing completion of the alkanols reaction. Polyvinyl alcohols are commercially available from DuPont and others. The preferred polyvinyl alcohol has a degree of hydrolysis greater than 92.0%, preferably greater than 98.0%, most preferably greater than 98.5%. For the sprayable aqueous film-forming antimicrobial composition of the present invention particularly preferred a fully hydrolyzed polyvinyl alcohol having a degree of hydrolysis greater than 98.5% is used. The most preferred polyvinyl alcohol has a degree of hydrolysis greater than 98.5%.

The compositions according to the present invention are capable of forming a long-lasting persistent, continuous, uniform barrier film that is based upon polyvinyl alcohol when applied to the skin. The compositions have particular utility as barrier teat dips that are used prophylactically against mastitis.

The composition may be used for prophylactic treatment of a dairy animal's teats to provide a long lasting persistent protective germicidal barrier film that demonstrates persistence between milkings, and is controllably reproducible to yield a continuous, uniform persistent barrier. This treatment process entails milking the animal, coating the teats with the composition after milking, allowing the composition to dry and so also form a layer of persistent barrier film on the teats. The composition may be applied topically by painting, foaming, dipping or spraying, particularly preferred by spraying. Furthermore, use of the composition is not limited to use against mastitis, and the composition may be used generally to treat or protect against any infectious skin condition.

A composition capable of forming a long-lasting, persistent, continuous, uniform barrier film may contain from about 0.1% to about 10.0% by weight, preferably from about 1.0% to about 5.0% by weight and further preferred from about 2.0% to about 4.5% by weight of polyvinyl alcohol for use as the barrier forming agent.

Rheology Modifier and Tackifier

According to the present invention, in the sprayable aqueous antimicrobial film-forming composition hydrophobically-modified ethoxylated urethanes are comprised as rheology modifier and tackifier. Hydrophobically-modified ethoxylated urethanes are non-ionic associative thickeners and are obtained by reacting diisocyanates with diols and hydrophobic blocking components. In the polymer molecule a distinction can be made between the following three segments: i) hydrophobic terminal segments; ii) several hydrophilic segments, and iii) urethane groups. The polymer is end-capped with hydrophobic segments, preferably $C_2$ to $C_{40}$ hydrocarbons, further preferred linear or branched chain $C_2$ to $C_{40}$ alkyl groups, more preferred linear or branched chain $C_8$ to $C_{24}$ alkyl groups. Possible and preferred hydrophobic segments are, for example, octyl group, dodecyl group, myristyl group, cetyl group, oleyl group, stearyl group, dodecylphenyl group, octylphenyl group and nonylphenyl group. The decisive factor for the viscosity increase effect is that each molecule contains at least two terminal hydrophobic segments. The hydrophilic segments used are polyethers or polyesters. Examples are polyesters of maleic acid and ethylene glycol and polyethers, such as polyethylene glycol or polyethylene glycol derivatives. Polyethers are the preferred hydrophilic segments, as these polymers offer the best chemical resistance and hence the best viscosity stability during storage of the respective composition. The polymer chain is extended by polyisocyanates.

The hydrophobically-modified ethoxylated urethane which is preferably used herein is a polymer having polyethylene glycol building blocks and urethane building blocks, wherein the polymer chain is end-capped with hydrophobic groups, preferably a hydrocarbon moiety belonging to one of the following hydrocarbon classes: a $C_8$-$C_{40}$ linear alkyl, an aryl-substituted $C_2$-$C_{40}$ alkyl, a $C_2$-$C_{40}$ alkyl-substituted phenyl, a $C_8$-$C_{40}$ branched alkyl, a $C_8$-$C_{40}$ carbocyclic alkyl; and a $C_8$-$C_{80}$ complex ester, in particular preferred selected from the group linear or branched chain $C_8$-$C_{22}$ alkyl groups, $C_8$-$C_{22}$ arylalkyl groups, $C_8$-$C_{22}$ alkylaryl groups.

Preferred hydrophobic groups are linear or branched alkyl groups having about 8 to about 40 carbon atoms such as capryl ($C_8$) group, isooctyl (branched $C_8$) group, nonyl ($C_9$) group, decyl ($C_{10}$) group, undecyl ($C_{11}$) group, lauryl ($C_{12}$) group, tridecyl ($C_{13}$) group, myristyl ($C_{14}$) group, pentadecyl ($C_{15}$) group, cetyl ($C_{16}$) group, cetearyl ($C_{16}$-$C_{18}$) group, palmitoleyl ($C_{16}$) group, heptadecyl ($C_{17}$) group, stearyl ($C_{18}$) group, isostearyl (branched $C_{18}$) group, nonadecyl ($C_{19}$) group, arachidyl ($C_{20}$) group, heneicosyl ($C_{21}$) group, behenyl ($C_{22}$) group, lignoceryl ($C_{24}$) group, ceryl ($C_{26}$) group, montanyl ($C_{28}$) group, melissyl ($C_{30}$) group, lacceryl (032) group, oleyl group, methyl ricinoleate, preferably n-octyl group, n-dodecyl group, iso-tridecyl group, myristyl group, cetyl group, oleyl group, stearyl group, octylphenyl group, nonylphenyl group and dodecylphenyl group.

In other embodiments the hydrophobic groups are linear and branched alkyl groups having about 8 to about 40 carbon atoms that are derived from a natural source include, without being limited thereto, alkyl groups derived from hydrogenated peanut oil, soybean oil and canola oil (all predominately $C_{18}$), hydrogenated tallow oil ($C_{16}$-$C_{18}$), and the like; and hydrogenated $C_{10}$-$C_{30}$ terpenols, such as hydrogenated geraniol (branched $C_{10}$), hydrogenated farnesol (branched Cis), hydrogenated phytol (branched $C_{20}$), and the like.

Other preferred hydrophobic groups are $C_2$-$C_{40}$ alkyl-substituted phenyl groups which include octylphenyl, nonylphenyl, decylphenyl, dodecylphenyl, hexadecylphenyl, octadecylphenyl, isooctylphenyl, sec-butylphenyl, and the like.

Further preferred hydrophobic groups are $C_8$-$C_{40}$ carbocylic alkyl groups which include, without being limited thereto, groups derived from sterols from animal sources, such as cholesterol, lanosterol, 7-dehydrocholesterol, and the like; from vegetable sources, such as phytosterol, stigmasterol, campesterol, and the like; and from yeast sources, such as ergosterol, mycosterol, and the like. Other carbocyclic alkyl hydrophobic end groups useful in the present invention include, without being limited thereto, cyclooctyl, cyclododecyl, adamantyl, decahydronaphthyl, and groups derived from natural carbocyclic materials such as pinene, hydrogenated retinol, camphor, isobornyl alcohol, and the like.

Exemplary aryl-substituted $C_2$-$C_{40}$ alkyl groups include, without limitation thereto, styryl (e.g., 2-phenylethyl), distyryl (e.g., 2,4-diphenylbutyl), tristyryl (e.g., 2,4,6-triphenylhexyl), 4-phenylbutyl, 2-methyl-2-phenylethyl, tristyrylphenolyl, and the like.

Non-limiting examples of suitable 08-080 complex esters include hydrogenated castor oil (predominately the triglyceride of 12-hydroxystearic acid); 1,2-diacyl glycerols such as 1,2-distearyl glycerol, 1,2-dipalmityl glycerol, 1,2- dimyristyl glycerol, and the like; di-, tri-, or poly-esters of sugars such as 3,4,6-tristearyl glucose, 2,3-dilauryl fructose, and the like; and sorbitan esters.

In another preferred embodiment the hydrophobically-modified ethoxylated urethane is a polymer having polyethylene glycol building blocks and urethane building blocks, wherein the polymer chain is end-capped with hydrophobic groups and wherein the urethane building blocks are formed by the use of diisocyante monomers in the polymerization reaction selected from the group consisting of m/p-tetramethylenexylylene diisocyanate, trimethylhexamethylene diisocyanate, 4/2,4'-diphenylmethane diisocyanate, 1,4-tetramethylene diisocyanate, 1,6-hexamethylene diisocyanate ("HDI"), 1,10-decamethylene diisocyanate, 1,4-cyclohexylene diisocyanate, 4,4'-methylenebis(isocyanatocyclohexane), 1-isocyanato-3-isocyanatom ethyl-3,5,5-trimethylcyclohexane (isophorone diisocyanate), m- and p-phenylene diisocyanate, 2,6- and 2,4-tolylene diisocyanate ("TDI"), xylene diisocyanate, 4-chloro-1,3-phenylene diisocyante, 4,4'-biphenylene diisocyanate, 4,4'-methylene diphenylisocyante ("MDI"), 1,5-naphthylene diisocyanate, 1,5-tetrahydronaphthylene diisocyanate and tetramethylxylene diisocyanate.

In still another preferred embodiment the hydrophobically-modified ethoxylated urethane is a polymer having polyethylene glycol segments and urethane segments, wherein the polymer chain is end-capped with hydrophobic segments and wherein the polyethylene glycol building blocks used have molecular weights from 1500 to 10000 daltons, preferably 3000 to 10000 daltons, more preferred 4500 to 7500 daltons and still further preferred 6000 to 7500 daltons. Suitable hydrophobically-modified ethoxylated urethanes (HEUR) are commercially available under the tradenames TAFIGEL® PUR (Münzing Chemie GmbH), Rheovis® PU, Rheovis® PE (BASF), Acrysol®, Acusol®880 and Acusol®882 (Rohm&Haas).

Antimicrobial Agents

Antimicrobial agents are the components of a composition that destroy microorganisms or prevent or inhibit their replication. In one aspect, only one type of antimicrobial agent may be used in the composition of the present invention. In another preferred aspect, the combined use of antimicrobial agents of different chemical classes or structures may be used, for example, to achieve an effective kill at lower concentrations of traditional antimicrobial agents.

Compositions of the present invention include at least one antimicrobial agent. In a preferred embodiment of the present invention the antimicrobial agent is selected from the group consisting of $I_2$, an iodophor, in particular in the form of polyvinyl pyrrolidone iodine (PVP-iodine), linear or branched chain aliphatic $C_4$-$C_{10}$ carboxylic acid, in particular capric and caprylic acids, octanoic acid, nonanoic acid, decanoic acid; lactic acid, salicylic acid, peroxycarboxylic acid, sulfoperoxycarboxylic acid, $C_1$-$C_4$ alkanols, isopropyl alcohol, benzyl alcohol, bronopol (2-bromo-2-nitro-1,3-propanediol), sodium pyridinathione, chlorohexidine, chlorhexidine diacetate, chlorohexidine digluconate, quaternary ammonium compounds such as the salts of alkyl dimethylbenzyl ammonium, dialkyl dimethyl ammonium compounds and benzethonium; sulfonic acids, hypohalous acid, alkali hypohalites, chlorine dioxide precursors, chlorine-releasing agents (particularly sodium hypochlorite and, more recently, chlorinated isocyanurates), hypochlorites, chlorine dioxide, chlorinated isocyanurates (chlorinated-S-triazene-trione), bromine, hydroxyquinone, ammonium chloride, hexachlorophene, diaphene, cetyl pyridinium chloride, acid anionics (e.g. alkylaryl sulfonic acids, aryl sulfonic acid, alkyl sulfonic acids, alkylaryl sulfuric acid, aryl sulfuric acid, alkyl sulfuric acid, alkylaryl sulfuric acid), phenolic antimicrobial agents may be chosen from ortho-phenyl phenol, 2,4,4'-trichloro-2"-hydroxydiphenylether, 4-chloro-3,5-dimethyl phenol, polyhexamethyl biguanide (CAS 32289-58-0), guanidine salts such as polyhexamethylene guanidine hydrochloride (CAS 57028-96-3), polyhexamethylene guanidine hydrophosphate (89697-78-9), and poly[2-(2-ethoxy)-ethoxyethyl]-guanidinium chloride (CAS 374572-91-5) and mixtures thereof.

In another preferred embodiment the aqueous antimicrobial film-forming composition according to the present invention comprises as antimicrobial agent an iodophor, in particular in the form of polyvinyl pyrrolidone iodine (PVP-iodine), and at least one further antimicrobial agent is comprised selected from the group consisting of linear or branched chain aliphatic $C_4$-$C_{10}$ carboxylic acid, in particular capric and caprylic acids, octanoic acid, nonanoic acid, decanoic acid; lactic acid, salicylic acid, peroxycarboxylic acid, sulfoperoxycarboxylic acid, $C_1$-$C_4$ alkanols, isopropyl alcohol, benzyl alcohol, bronopol (2-bromo-2-nitro-1,3-propanediol), sodium pyridinathione, chlorohexidine, chlorhexidine diacetate, chlorohexidine digluconate, quaternary ammonium compounds such as the salts of alkyl dimethylbenzyl ammonium, dialkyl dimethyl ammonium compounds and benzethonium; sulfonic acids, hypohalous acid, alkali hypohalites, chlorine dioxide precursors, chlorine-releasing agents (particularly sodium hypochlorite and, more recently, chlorinated isocyanurates), hypochlorites, chlorine dioxide, chlorinated isocyanurates (chlorinated-S-triazene-trione), bromine, hydroxyquinone, ammonium chloride, hexachlorophene, diaphene, cetyl pyridinium chloride, acid anionics (e.g. alkylaryl sulfonic acids, aryl sulfonic acid, alkyl sulfonic acids, alkylaryl sulfuric acid, aryl sulfuric acid, alkyl sulfuric acid, alkylaryl sulfuric acid), phenolic antimicrobial agents may be chosen from ortho-phenyl phenol, 2,4,4'-trichloro-2"-hydroxydiphenylether, 4-chloro-3,5-dimethyl phenol, polyhexamethyl biguanide (CAS 32289-58-0), guanidine salts such as polyhexamethylene guanidine hydrochloride (CAS 57028-96-3), polyhexamethylene guanidine hydrophosphate (89697-78-9), and poly[2-(2-ethoxy)-ethoxyethyl]-guanidinium chloride (CAS 374572-91-5) and mixtures thereof.

As mentioned above, the preferred antimicrobial agent is an iodophor and particularly preferred the iodine compound is provided in the form of polyvinyl pyrrolidone iodine (PVP-iodine).

Iodine Compound

The iodine compounds of the invention provide a portion of the antimicrobial activity of the compositions of the invention and are selected to provide disinfecting or sanitizing antimicrobial efficacy. Iodine compounds suitable for a composition of the invention are known and disclosed in, for example, U.S. Pat. Nos. 4,271,149; 5,310,549; 5,368,868; and 5,503,838, the entire disclosures of which are incorporated herein by reference.

The most preferred antimicrobial agent used in the compositions hereof is in the form of iodine, with an average available (titratable) iodine level of from about 0.05% to 2.0% by weight on a nominal basis, and more preferably from about 0.1% to 1.0% by weight. In preferred embodiments, the iodine compound can be present in the form of an iodophor. That is, the iodine compound is present as a complex with one or more suitable surfactants, or other suitable complexing compound, such as, for example, polyvinyl pyrrolidone (PVP). Typically, the iodophor can be present in a composition of the invention to provide approximately 500 ppm to 6000 ppm, preferably about 1000 ppm to 3000 ppm, of free iodine in the working composition. Iodophors are known and disclosed in, for example, U.S. Pat. Nos. 5,618,841, 5,310,549, etc. The entire disclosure of each of these patents is incorporated herein by reference. Preferred surfactants suitable for preparing an iodophor with one or more surfactants are further discussed below.

In one embodiment, the present invention provides an antiseptic composition that includes: an antimicrobial agent selected from the group consisting of iodine (I2), an iodophor i.e., a complex of iodine or triiodide with a carrier that is capable of generating elemental iodine under use conditions, such as povidone-iodine, and combinations thereof, wherein the antimicrobial agent is present in an amount sufficient to provide an available iodine concentration of about 0.05 wt.-% to 2.0 wt.-%, preferably from 0.1 wt.-% to 1.0 wt.-%.

The complexed iodine of the invention is preferably prepared through the use of iodine and complexing agent selected from the group consisting of ethoxylated surfactants, cellulose, cellulose derivatives and the polyvinyl pyrrolidone component. The alkoxylated (usually ethoxylated) surfactants include, but are not limited to, the group consisting of alkylphenol ethoxylates, ethoxylated fatty acids, alcohol ethoxylates, alcohol alkoxylates, polysorbates (ethoxylated sorbitol) and ethylene oxide-propylene oxide copolymers (Poloxamers). Preferred Poloxamer surfactants are those described in U.S. Pat. No. 5,368,868, which is incorporated by reference herein. These surfactants include a polyoxypropylene moiety having an average molecular weight in excess of 2600, and more preferably from about 2600-4000. The polyoxyethylene content typically ranges from about 30.0 to 75.0% by weight, and more preferably from about 40.0 to 70.0% by weight. Generally speaking, the complexing agents would be used at a level of from about 0.4 to 10.0% by weight, and more preferably from about 0.4 to 4.0% by weight.

In a particularly preferred embodiment the antimicrobial agent iodine is provided in the form of a complex with polyvinyl pyrrolidone. The polyvinyl pyrrolidone component is preferably taken from the group of K-30 through K-90 povidones. The PVP primarily serves as iodine complexing agent and therefore as antimicrobial agent but may also serve as film-forming agent alone or with other film-forming agents or film-forming polymers. Levels of use are typically from about 0.5 to 5.0% by weight PVP, and more preferably from about 1.0 to 2.5% by weight. When iodine is used as the antimicrobial agent, the PVP can serve two functions, i.e., as a film former and as an iodine complexor.

Anionic Surfactants

Anionic surfactants useful in the present invention have maximum biocidal activity and/or biostatis against mastitis-causing organisms at a pH in the range of 2.0 to 5.0. Hence, these surfactants are generally present in the present compositions in the range from 0.05 wt.-% to 5.0% wt.-%, preferably from 0.1 wt.-% to 2.0% wt.-%.

Preferred anionic surfactants can be chosen from a linear alkylbenzene sulfonic acid, a linear alkylbenzene sulfonate, an alkyl α-sulfomethyl ester, an α-olefin sulfonate, an alcohol ether sulfate, an alkyl sulfate, an alkylsulfo succinate, a dialkylsulfo succinate, and alkali metal, alkaline earth metal, amine and ammonium salts thereof. Specific examples preferred are linear $C_{10}$-$C_{16}$ alkylbenzene sulfonic acid, linear $C_{10}$-$C_{16}$ alkylbenzene sulfonate or alkali metal, alkaline earth metal, amine and ammonium salt thereof e.g. sodium dodecylbenzene sulfonate, sodium $C_{14}$-$C_{16}$ α-olefin sulfonate, sodium methyl a-sulfomethyl ester and disodium methyl α-sulfo fatty acid salt.

Linear alkylbenzene sulfonates, or linear alkylbenzene sulfonic acids, (hereafter sometimes collectively referred to as "LAS") are moderately effective bactericides, particularly in mildly acidic media. However, linear alkylbenzene sulfonic acids are generally more active against gram positive organisms such as *Staphylococcus aureus* than against gram negative organisms, particularly at "skin" pH, i.e., greater than 5.0. These microorganisms may have as their origin, water, soil, improperly cleaned utensils, manure, infected cows, human hands, etc. For the most part, gram positive organisms such as *Staphylococcus aureus* originate in mammals (including humans), while many gram negative organisms are found in the feces of animals as well as humans. Linear alkylbenzene sulfonates are a useful class of anionic surfactants which appear to provide activity against both gram positive microorganisms (e.g., *S. aureus*) as well as gram negative microorganisms (e.g., *Pseudomonas aeruginosa*). LAS are not necessary to provide acceptable biocidal results in the composition of the invention, however it improves the antimicrobial effect of the composition of the present invention. With respect to the linear alkyl chain of the LAS, it should not be so long as to create incompatibility with water yet not so short so as to reduce antimicrobial action. Therefore, the alkyl chains should preferably be 9 to 18, preferably 10 to 16, more preferably 10 to 13 carbon atoms in length. In a preferred embodiment dodecyl benzyl sulfonic acid is used. In a preferred embodiment of the present invention the alkylbenzene sulfonic acid is $C_{9-18}$ alkylbenzene sulfonic acid, further preferred $C_{10-16}$ alkylbenzene sulfonic acid, more preferred $C_{10-13}$ alkylbenzene sulfonic acid. Further preferred, the alkylbenzene sulfonic acid is linear alkylbenzene sulfonic acid, more preferably linear $C_{10-13}$ alkylbenzene sulfonic acid. In a particular preferred embodiment the alkylbenzene sulfonic acid is linear straight chain alkylbenzene sulfonic acid in which the average number of carbon atoms in the alkyl group is from 10 to 13. In another particular preferred embodiment the alkylbenzene sulfonic acid is linear straight chain alkylbenzene sulfonic acid in which at least 95.0 wt.-% of the alkylbenzene sulfonic acid has 10 to 13 carbon atoms in the alkyl group. A preferred alkylbenzene sulfonic acid is commercially available as MARLON® AS 3 (Sasol Germany GmbH, Marl, Germany). Preferably, the composition of the present invention comprises from 0.05 wt.-% to 5.0 wt.-%, further preferred from 0.1 wt.-% to 2.0 wt.-%, and particularly preferred from 0.1 wt.-% to 0.5 wt.-% of alkylbenzene sulfonic acid, preferably $C_{9-18}$ alkylbenzene sulfonic acid, further preferred $C_{10-16}$ alkylbenzene sulfonic acid, more preferred $C_{10-13}$ alkylbenzene sulfonic acid; still further preferred linear alkylbenzene sulfonic acid, more preferably linear $C_{10-13}$ alkylbenzene sulfonic acid; in particular linear straight chain alkylbenzene sulfonic acid in which the average number of carbon atoms in the alkyl group is from 10 to 13, preferably from 0.05 wt.-% to 5.0 wt.-%, further preferred from 0.1 wt.-% to 2.0 wt.-%, and particularly preferred from 0.1 wt.-% to 0.5 wt.-% of $C_{10}$-$C_{13}$ alkylbenzene sulfonic acid.

Percarboxylic Acids

The sprayable aqueous antimicrobial film-forming composition according to the present invention may also comprise as antimicrobial agent a peracid, also referred to as peroxycarboxylic acid, which exists as chemical equilibrium consisting of a peracid, the corresponding carboxylic acid, hydrogen peroxide and water.

Generally when the peroxycarboxylic acid is formulated in accordance with the invention a mono carboxylic acid, such as acetic acid, is combined with an oxidizer such as hydrogen peroxide. The result of this combination is a reaction producing a peroxycarboxylic acid, such as peroxyacetic acid, and water. The reaction follows an equilibrium in accordance with the following equation:

$$H_2O_2 + RCOOH \rightleftharpoons RCOOOH + H_2O$$

wherein the $K_{eq}$ is 2.0.

The importance of the equilibrium stems from the presence of hydrogen peroxide, the carboxylic acid and the peroxycarboxylic acid in the same composition at the same time. This combination provides enhanced sanitizing compared to carboxylic acid alone.

The first constituent of the equilibrium mixture comprises one or more carboxylic acids. The carboxylic acids function as a precursor for the reaction product peroxycarboxylic acid while providing a source of acidity and antimicrobial efficacy. The acidity stabilizes and otherwise assists in maintaining the equilibrium concentration of the peroxycarboxylic acid.

The other principle component of the antimicrobial composition of the invention is an oxidized carboxylic acid. This oxidized or peroxycarboxylic acid provides heightened antimicrobial efficacy when combined with hydrogen peroxide and the monocarboxylic acid in an equilibrium reaction mixture. Generally, any number of peroxycarboxylic acids is useful in accordance with the method of the invention.

The peracid is present at an amount sufficient to exhibit antimicrobial activity. A variety of peroxycarboxylic acids may be employed in the compositions according to the invention. According to a preferred embodiment of the invention suitable peroxycarboxylic acids include ester peroxycarboxylic acids, alkyl ester peroxycarboxylic acids, and/or combinations of several different peroxycarboxylic acids, as described herein.

The aqueous antimicrobial composition according to the present invention includes at least one percarboxylic acid. In some embodiments, the compositions of the present invention include at least two or more percarboxylic acids.

In a preferred embodiment of the present invention the composition comprises a peracid selected from:

a) peracids corresponding to general formula (I) $R^1—O_2C—(CH_2)_p—CO_3H$, wherein $R^1$ is hydrogen or an alkyl group containing 1 to 4 carbon atoms and p is an integer from 1 to 4, or salts thereof;

b) phthalimidopercarboxylic acids (II) wherein the percarboxylic acid contains 1 to 18 carbon atoms, or salts thereof;

c) compounds corresponding to formula (III) $R^2—CO_3H$, wherein $R^2$ is an alkyl or alkenyl group containing 1 to 22, preferably 1 to 18 carbon atoms.

In yet a further preferred embodiment of the composition comprises a peracid selected from:

a) peracids corresponding to general formula (I) $R^1—O_2C—(CH_2)_p—CO_3H$, wherein $R^1$ is hydrogen or methyl group and p is an integer from 1 to 4, or salts thereof;

b) phthalimidopercarboxylic acids (II) wherein the percarboxylic acid contains 1 to 8 carbon atoms, or salts thereof;

c) compounds corresponding to formula (III) $R^2—CO_3H$, wherein $R^2$ is an alkyl or alkenyl group containing 1 to 12 carbon atoms.

Further preferred, the peracid is selected from peracetic acid, perpropionic acid, peroctanoic acid, phthalimidoperhexanoic acid, phthalimidoperoctanoic acid, persuccinic acid, persuccinic acid monomethyl ester, perglutaric acid, perglutaric acid monomethyl ester, peradipic acid, peradipic acid monomethyl ester, persuccinic acid, and persuccinic acid monomethyl ester.

In still further preferred embodiments, the carboxylic acid for use with the compositions of the present invention in order to provide the corresponding peroxycarboxylic acid includes a $C_1$ to $C_{22}$ carboxylic acid. In an aspect, any suitable $C_1$-$C_{22}$ carboxylic acid can be used in the present compositions. In some embodiments, the $C_1$-$C_{22}$ carboxylic acid is a $C_2$-$C_{20}$ carboxylic acid. In other embodiments, the $C_1$-$C_{22}$ carboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ carboxylic acid. Further preferred the carboxylic acid for use with the compositions of the present invention is a $C_1$ to $C_{18}$ more preferred a $C_1$ to $C_{12}$ carboxylic acid. The carboxylic acid for use with the compositions of the present invention in particular may be a $C_5$ to $C_{12}$ carboxylic acid. In particular preferred embodiments, the carboxylic acid for use with the compositions of the present invention is a $C_1$ to $C_4$ carboxylic acid. Examples of suitable carboxylic acids include, but are not limited to, formic, acetic, propionic, butanoic, pentanoic, hexanoic, heptanoic, octanoic, nonanoic, decanoic, undecanoic, dodecanoic, as well as their branched chain isomers, lactic, maleic, ascorbic, citric, hydroxyacetic, neopentanoic, neoheptanoic, neodecanoic, oxalic, malonic, succinic, glutaric, adipic, pimelic, suberic, sebacid acid, and mixtures thereof. A particularly preferred carboxylic acid is acetic acid. The compositions may utilize a combination of several different carboxylic acids. In some preferred embodiments, the composition includes one or more $C_1$ to $C_4$ carboxylic acids and one or more $C_5$ to $C_{12}$ carboxylic acids. In further preferred embodiments, the $C_1$ to $C_4$ carboxylic acid is acetic acid and the $C_5$ to $C_{12}$ acid is octanoic acid.

Corresponding to the carboxylic acid the aqueous antimicrobial composition of the present invention comprises include at least one peroxycarboxylic acid. In preferred embodiments, the peroxycarboxylic acid for use with the compositions of the present invention includes a $C_1$ to $C_{22}$ peroxycarboxylic acid. In an aspect, any suitable $C_1$-$C_{22}$ percarboxylic acid can be used in the present compositions. In some embodiments, the $C_1$-$C_{22}$ percarboxylic acid is a $C_2$-$C_{20}$ percarboxylic acid. In other embodiments, the $C_1$-$C_{22}$ percarboxylic is a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, or $C_{22}$ percarboxylic acid. Further preferred the peroxycarboxylic acid for use with the compositions of the present invention is a $C_1$ to $C_{18}$, more preferred a $C_1$ to $C_{12}$ peroxycarboxylic acid. The peroxycarboxylic acid for use with the compositions of the present invention in particular may be a $C_5$ to $C_{12}$ peroxycarboxylic acid. In particular preferred embodiments, the peroxycarboxylic acid for use with the compositions of the present invention is a $C_1$ to $C_4$ peroxycarboxylic acid. Peroxycarboxylic acids useful in the compositions include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, or the peroxyacids of their branched chain isomers, peroxylactic, peroxymaleic, peroxyascorbic, peroxycitric, peroxyhydroxyacetic, peroxyneopentanoic, peroxyneoheptanoic, peroxyneodecanoic, peroxyoxalic, peroxymalonic, peroxysuccinic, peroxyglutaric, peroxyadipic, peroxypimelic, peroxysuberic, peroxysebacid acid and mixtures thereof. A particularly preferred peroxycarboxylic acid is peroxyacetic acid. The compositions may utilize a combination of several different peroxycarboxylic acids. In some preferred embodiments, the composition includes one or more $C_1$ to $C_4$ peroxycarboxylic acids and one or more $C_5$ to $C_{12}$ peroxycarboxylic acids. In further preferred embodiments, the $C_1$ to $C_4$ peroxycarboxylic acid is peroxyacetic acid and the $C_5$ to $C_{12}$ acid is peroxyoctanoic acid.

In preferred embodiments, the compositions include peroxyacetic acid. Peroxyacetic (or peracetic) acid is a peroxycarboxylic acid having the formula: $CH_3COOOH$. Generally, peroxyacetic acid is a liquid having an acrid odor at higher concentrations and is freely soluble in water, alcohol, ether, and sulfuric acid. Peroxyacetic acid can be prepared through any number of methods known to those of skill in the art including preparation from acetaldehyde and oxygen in the presence of cobalt acetate. A solution of peroxycarboxylic acid can be obtained by combining the corresponding carboxylic acid with hydrogen peroxide. A solution of peroxyacetic acid can be obtained by combining acetic acid with hydrogen peroxide. A 50% solution of peroxyacetic acid can be obtained by combining acetic anhydride, hydrogen peroxide and sulfuric acid.

In preferred embodiments, the compositions include peroxyoctanoic acid, peroxynonanoic acid, or peroxyheptanoic acid. In further preferred embodiments, the compositions include peroxyoctanoic acid. Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid can be prepared through any number of methods known to those of skill in the art. A solution of peroxyoctanoic acid can be obtained by combining octanoic acid and hydrogen peroxide and a hydrotrope, solvent or carrier.

Useful peroxycarboxylic acids also include the ester peroxycarboxylic acids described herein and compositions of the present invention including those ester peroxycarboxylic acids. Peroxy forms of carboxylic acids with more than one carboxylate moiety can have one or more of the carboxyl moieties present as peroxycarboxyl moieties. These peroxycarboxylic acids have been found to provide good antimicrobial action with good stability in aqueous mixtures. In a preferred embodiment, the composition of the invention utilizes a combination of several different peroxycarboxylic acids. Examples of suitable alkyl ester carboxylic acids include monomethyl oxalic acid, monomethyl malonic acid, monomethyl succinic acid, monomethyl glutaric acid, monomethyl adipic acid, monomethyl pimelic acid, monomethyl suberic acid, and monomethyl sebacic acid; monoethyl oxalic acid, monoethyl malonic acid, monoethyl succinic acid, monoethyl glutaric acid, monoethyl adipic acid, monoethyl pimelic acid, monoethyl suberic acid, and monoethyl sebacic acid; monopropyl oxalic acid, monopropyl malonic acid, monopropyl succinic acid, monopropyl glutaric acid, monopropyl adipic acid, monopropyl pimelic acid, monopropyl suberic acid, and monopropyl sebacic acid, in which propyl can be n- or isopropyl; and monobutyl oxalic acid, monobutyl malonic acid, monobutyl succinic acid, monobutyl glutaric acid, monobutyl adipic acid, monobutyl pimelic acid, monobutyl suberic acid, and monobutyl sebacic acid, in which butyl can be n-, iso-, or t-butyl.

In a further preferred embodiment the aqueous antimicrobial composition comprises 0.01 wt.-% to 10.0 wt.-% of peracid. Further preferred, the composition additionally contains 0.01 to 18.0 wt.-% of hydrogen peroxide. Still further preferred, the composition comprises at least a mixture of hydrogen peroxide, peracid and the corresponding carboxylic acid. Most preferred, the composition comprises at least hydrogen peroxide, peroxyacetic acid and acetic acid. In further preferred embodiments, the aqueous antimicrobial compositions of the present invention comprises 0.01 wt.-% to 10.0 wt.-% of peroxyacetic acid. As the peracid, also referred to as peroxycarboxylic acid, exists as chemical equilibrium consisting of a peracid, the corresponding carboxylic acid, hydrogen peroxide and water, the quantity given as "0.01 wt.-% to 10.0 wt.-% of peracid" or given as "0.01 wt.-% to 10.0 wt.-% of peroxyacetic acid" means "0.01 wt.-% to 10.0 wt.-% of peracid and 0.000 wt.-% to 20.0 wt.-% of the corresponding carboxylic acid" and "0.01 wt.-% to 10.0 wt.-% of peroxyacetic acid and 0.000 wt.-% to 20.0 wt.-% of acetic acid", respectively.

As one skilled in the art shall appreciate, peroxycarboxylic acids are not as stable as carboxylic acids, their stability generally increases with increasing molecular weight. Thermal decomposition of these acids can generally proceed by free radical and nonradical paths, by photodecomposition or radical-induced decomposition, or by the action of metal ions or complexes. Percarboxylic acids can be made by the direct, acid catalyzed equilibrium action of hydrogen peroxide with the carboxylic acid, by autoxidation of aldehydes, or from acid chlorides, and hydrides, or carboxylic anhydrides with hydrogen or sodium peroxide.

Making the Peroxycarboxylic Acids

Exemplary methods and apparatus for making peroxycarboxylic acids are disclosed in U.S. Pat. Nos. 7,547,421 and 8,017,082, both entitled "Apparatus and Method for Making a Peroxycarboxylic Acid," hereby expressly incorporated herein in its entirety by reference. These and other known methods and apparatus for making the particular peroxycarboxylic acids used according to the invention are included within the scope of the invention.

In some aspects, at ambient conditions, the reaction to make the peroxycarboxylic acid compositions may take a week or more to reach the desirable concentrations of peroxycarboxylic acid at equilibrium. In other aspects conditions can be modified to reach maximum peroxycarboxylic acid compositions within about 60 minutes or within a few hours. One skilled in the art will ascertain the various modifications to the conditions of the peroxycarboxylic acid reactions in order to obtain the desirable concentrations within a particular amount of time.

Sulfoperoxycarboxylic Acids

As used herein, the term "sulfoperoxycarboxylic acid" or "sulfonated peroxycarboxylic acid" refers to the peroxycarboxylic acid form of a sulfonated carboxylic acid. The sulfoperoxycarboxylic acids can be used alone as antimicrobial agent, or can be combined with other antimicrobial agents.

Sulfoperoxycarboxylic acid, sulfonated peroxycarboxylic acid and/or derivatives thereof that can be used as antimicrobial agent according to the present invention are described in the international application WO 2009/118714 A2 which is completely included by reference.

In preferred embodiments of the present invention sulfoperoxycarboxylic acid of the following formula: $R^3$—CH$(SO_3^-X^+)R^4$—COOOH, wherein $R^3$ is hydrogen, or a substituted or unsubstituted alkyl group; $R^4$ is a substituted or unsubstituted alkyl group; X is hydrogen, a cationic group, or an ester forming moiety; or salts or esters thereof.

In some embodiments, $R^3$ is a substituted or unsubstituted $C_m$ alkyl group; X is hydrogen a cationic group, or an ester forming moiety; $R^4$ is a substituted or unsubstituted Cn alkyl group; m=1 to 10; n=1 to 10; and m+n is less than 18, or salts, esters or mixtures thereof.

In some embodiments, $R^3$ is hydrogen. In other embodiments, $R^3$ is a substituted or unsubstituted alkyl group. In some embodiments, $R^3$ is a substituted or unsubstituted alkyl group that does not include a cyclic alkyl group. In some embodiments, $R^3$ is a substituted alkyl group. In some embodiments, $R^3$ is an unsubstituted $C_1$-$C_9$ alkyl group. In some embodiments, $R^3$ is an unsubstituted $C_7$ or $C_8$ alkyl. In other embodiments, $R^3$ is a substituted $C_8$-$C_{10}$ alkyl group. In some embodiments, $R^3$ is a substituted $C_8$-$C_{10}$ alkyl group which is substituted with at least 1, or at least 2 hydroxyl groups. In still yet other embodiments, $R^3$ is a substituted $C_1$-$C_9$ alkyl group. In some embodiments, $R^3$ is a substituted $C_1$-$C_9$ substituted alkyl group which is substituted with at least 1 $SO_3H$ group.

In other embodiments, $R^3$ is a $C_9$-$C_{10}$ substituted alkyl group. In some embodiments, $R^3$ is a substituted $C_9$-$C_{10}$ alkyl group wherein at least two of the carbons on the carbon backbone form a heterocyclic group. In some embodiments, the heterocyclic group is an epoxide group.

In some embodiments, $R^4$ is a substituted $C_1$-$C_{10}$ alkyl group. In some embodiments, $R^4$ is a substituted $C_8$-$C_{10}$ alkyl. In some embodiments, $R^4$ is an unsubstituted $C_6$-$C_9$ alkyl. In other embodiments, $R^4$ is a $C_8$-$C_{10}$ alkyl group substituted with at least one hydroxyl group. In some embodiments, $R^4$ is a $C_{10}$ alkyl group substituted with at least two hydroxyl groups. In other embodiments, $R^4$ is a $C_8$ alkyl group substituted with at least one $SO_3H$ group. In some embodiments, $R^4$ is a substituted $C_9$ group, wherein at least two of the carbons on the carbon backbone form a heterocyclic group. In some embodiments, the heterocyclic group is an epoxide group.

In some embodiments, $R^3$ is a $C_8$-$C_9$ substituted or unsubstituted alkyl, and $R^4$ is a $C_7$-$C_8$ substituted or unsubstituted alkyl.

In some embodiments, the compound of the invention is selected from the group consisting of:
10-hydroxy-9-sulfooctadecaneperoxoic acid;
9, 10-dihydroxy-8-sulfooctadecaneperoxoic acid;
9-sulfooctadecaneperoxoic acid;
11-sulfoundecaneperoxoic acid;
10, 11-disulfoundecaneperoxoic acid;
8-(3-octyloxiran-2-yl)-8-sulfooctaneperoxoic acid;
9, 10-dihydroxy-11-sulfooctadecaneperoxoic acid;
9-(1-sulfoheptyloxiran-2-yl)-9-nonaneperoxoic acid;
9-hydroxy-10-sulfooctadecaneperoxoic acid;
10-sulfooctadecaneperoxoic acid;
9,10-disulfooctadecaneperoxoic acid;
10-sulfoundecaneperoxoic acid;
9-(3-octyloxiran-2-yl)-9-sulfononaneperoxoic acid;
10, 11-dihydroxy-9-sulfooctadecaneperoxoic acid;
8,9-dihydroxy-10-sulfooctadecaneperoxoic acid;

In some embodiments, the antimicrobial agent for the preparation of a peroxycarboxylic fatty acid can be a sulfonated fatty acid. Sulfonated fatty acids suitable for use as antimicrobial agent include, but are not limited to, 11-sulfoundecanoic acid, 10,11-disulfoundecanoic acid, sulfonated oleic acid, sulfonated linoleic acid, sulfonated palmitic acid and sulfonated stearic acid.

The sulfoperoxy acids can be formed using a variety of reaction mechanisms. For example, in some embodiments, the peracids are formed by the direct acid catalyzed equilibrium action of hydrogen peroxide with the materials.

Polyoxyalkylene Ether Carboxylic Acids/Alkylether Carboxylic Acids

Further compounds which may be used as surfactant in the composition of the present invention are polyoxyalkylene ether carboxylic acids. Therefore, in preferred embodiments of the composition according to the present invention polyoxyalkylene ether carboxylic acids, also termed alkyl ether carboxylic acids, in particular polyoxypropylene or polyoxyethylene ether carboxylic acids, are comprised. Polyoxypropylene or polyoxyethylene ether carboxylic acids, in particular polyoxyethylene ether carboxylic acids can be prepared by initially propoxylating or ethoxylating, respectively, the corresponding alkanols with the substituent R and reacting the propoxylates and ethoxylates, respectively, with chloroacetic acid. Since mixtures of propoxylating/ethoxylation products differing in their degrees of propoxylation/ethoxylation, rather than pure substances with a defined number of propoxy/ethoxy groups are obtained in the propoxylation/ethoxylation step, the ether carboxylic acids are generally corresponding mixed products. Further, products can be prepared having propoxy and ethoxy groups. Alkylether carboxylic acids in which the alkyl group R contains 4 to 8 carbon atoms are preferably used. The film-forming composition of the present invention preferably contains 0.5 to 2.0 wt.-% of polyoxyalkylene ether carboxylic acids. Preferably a mixture of polyoxyalkylene ether carboxylic acids are comprised in the composition of the present invention, in particular a mixture of Capryleth-9 Carboxylic acid (R—O—$(C_2H_4$—O$)_n$—$CH_2$—COOH; R=$C_8$ alkyl group; n is about 5; CAS No. 53563-70-5) and Buteth-2 Carboxylic Acid (R—O—$(C_2H_4$—O$)_n$—$CH_2$—COOH; R=$C_4$ alkyl group; n is about 2; CAS No. 75427-76-8) commercially available as Akypto® LF6 from KAO Chemicals.

In a preferred embodiment the composition is comprising polyoxypropylene alkylether carboxylic acid, in particular having the following formula R—O—$(C_3H_6$—O$)_m$—$(C_2H_4$—O$)_n$—$CH_2$—COOH; wherein R is an alkyl group having 4 to 10 carbon atoms, m is an integer from 0 to 8 and n is an integer from 0 to 8, wherein at least one of m or n is not 0.

Still further preferred the composition comprises polyoxyethylene alkylether carboxylic acid having the following formula R—O—$(C_2H_4$—O$)_n$—$CH_2$—COOH; wherein R is an alkyl group having 4 to 10 carbon atoms and n is an integer from 2 to 8.

Defoaming Agents

Generally, defoamers or anti-foaming agents which can be used in accordance with the invention include silica and silicones; aliphatic acids or esters; alcohols; sulfates or sulfonates; amines or amides; halogenated compounds such as fluorochlorohydrocarbons, vegetable oils, waxes, mineral oils as well as their sulfonated or sulfated derivatives; fatty acids and/or their soaps such as alkali, alkaline earth metal soaps; and phosphates and phosphate esters such as alkyl and alkaline diphosphates, and tributyl phosphates among others; and mixtures thereof.

One of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A®, DC-200m, Xiameter® ACP-0544 Antifoam from Dow Corning Corporation. These defoamers can be present at a concentration range from about 0.001 wt.-% to about 3.0 wt.-%, from about 0.005 wt.-% to about 1.0 wt.-%, from about 0.02 wt.-% to about 0.2 wt.-%.

Other defoamers that can be used in preferred embodiments of the invention include organic amides such as Antimussol® from Clariant or oil and/or polyalkylene based compounds such as Agitan® from Münzing or branched fatty alcohols such as Isofol® from Sasol.

The compositions of the present invention may further include antifoaming agents or defoaming agents which are based on alcohol alkoxylates that are stable in alkaline environments and are oxidatively stable. To this end one of the more effective antifoaming agents are the alcohol alkoxylates having an alcohol chain length of about $C_5$-$C_{12}$, and more specifically $C_9$-$C_{11}$, and having poly-propylene oxide alkoxylate in whole or part of the alkylene oxide portion. Commercial defoamers commonly available of this type include alkoxylates such as the BASF Degressal's; especially Degressal SD20.

Furthermore so called cloud point defoamers (typically non-ionic surfactants consisting of ethoxylated/propoxylated alcohols) may be used in the present invention such as Plurafac® types from BASF or Dehypon® types from Cognis.

Buffering and pH Adjusting Agents

The pH value of the composition may be selectively adjusted by the addition of acidic or basic ingredients. Generally, an acidic pH is preferred. Suitable acids for use as pH adjusting agents may include, for example, citric acid, acetic acid, lactic acid, phosphoric acid, phosphorous acid, sulfamic acid, nitric acid, nitrous acid and hydrochloric acid. It will be recognized by those skilled in the art that the organic acid, e.g., lactic acid, selected as the antimicrobial organic acid will also influence pH, and thus, have an adjusting effect as discussed in this paragraph. Mineral acids may be used to drastically lower the pH. The pH may be raised or made more alkaline by addition of an alkaline agent such as sodium hydroxide, potassium hydroxide, sodium carbonate, sodium bicarbonate, monosodium acid diphosphonate, triethanolamine or combinations thereof. Traditional acid buffering agents such as citric acid, lactic acid, phosphoric acid may also be used to maintain a desired pH. The pH value of the composition may be adjusted by the addition of acidic or basic or buffering materials.

The physical property of pH may be adjusted by acid or base addition, and is broadly preferred in the range of from 2.0 to 8.0 for use in teat dip compositions and other compositions that are intended to contact the skin. In a more preferred sense this range is from 2.0 to 5.5, further preferred from 2.0 to 5.0, and a still more preferred from 2.5 to 4.5.

Skin Conditioning Agents

Teat dip compositions of the present invention can also include an emollient, moisturizer, humectant or re-fatting agent to lubricate, condition and generally reduce irritation and promote the healing of the teat surface of which may result either from the antimicrobial component, from the mechanical action of the milking machine or from environmental conditions such as frigid temperatures wind chill, dehydration, abrasion, windburn and sunburn. Any water miscible, soluble or dispersible skin-conditioning agent may be used in this invention. Compositions such as polyhydric alcohols are useful in the invention including glycerin, sorbitol, mannitol, and propylene glycol and its homopolymers; polyethylene glycol (PEG) 200-10,000, polyethylene glycol esters, acyl lactylates, polyquaternium-7, glycerol cocoate/laurate, PEG-7 glycerol cocoate, stearic acid, hydrolyzed silk peptide, silk protein, guar hydroxypropyltrimonium chloride, alkyl poly glucoside/glyceryl laurate, shea butter and coco butter; fatty acid esters of simple monohydril alcohols including isopropyl palmitate or isopropyl myristate and similar esters; D-Panthenol; polyol esters of fatty acids; and, ethoxylated lanolins, vegetable oils, and similar natural sourced derivatives such as aloe; sunscreen agents, such as titanium dioxide, zinc oxide, octyl methoxycinnamate (OMC), 4-methylbenzylidene camphor (4-MBC), oxybenzone and homosalate; and itch-relief or numbing agents, such as aloe vera, calamine, mint, menthol, camphor, antihistamines, corticosteroids, benzocaine and paroxamine HCl. Preferred emollients to be used in the invention include glycerin, and propylene glycol and lanolin. It should be noted that preferably the freezing point depressant component in the carrier medium also act as emollient/moisturizer/humectants. For example, in some preferable embodiments, propylene glycol and glycerin are present in high concentrations in the composition, and act as both freezing point depressants and emollients.

Opacifying Agents and Dyes

The compositions can also include, dyes, pigments, marking agents, or other such components, as is generally known. An opacifying agent or dye is optionally included in the present compositions. For example, color on a teat tells a farmer that a particular cow has been treated. To preclude any problems with possible contamination of milk, it is preferred that only FD&C Certified (food grade) dyes be used such as, for example, tartrazine E102. Titanium dioxide ($TiO_2$) is widely used as an opacifier and can also be used in combination with various colorants.

EXAMPLES

The compositions and methods will be further illustrated by the following non-limiting examples.

Example 1: Formulations and Methods 1.1 Formulation

A series of antimicrobial teat dip formulations were prepared. The amount of each component to be added is set forth in the examples identified as formulations F1 to F9, A1 to A7 and F10 to F22 in Tables 1 to 4.

Unless otherwise specified, ingredient amounts reported in these tables are on the basis of weight percent to the total composition. The formulations were sprayed onto the teats of cows using a Jetstream Gun (AJS/2402) having a fixed nozzle tip with O-ring (AJS2415) from Ambic® (Ambic Equipment Limited, UK), which is a vacuum operated sprayer. After spraying the criteria relating to the quality of film formation, spray shadow and wetting on skin were evaluated. The results were summarized in Tables 1-4.

1.2 Comparative Film Evaluation

The quality of continuous and uniform film of the teat dip was evaluated by a method described as below. After the preparation of the compositions they were sprayed onto teats of cows. The film barrier quality and the wetting on skin was evaluated based on 3 and 2 scales, respectively. The numerical rating was as follows:

Film Formation

| | |
|---|---|
| −1 | insufficient film formation |
| 0 | moderate film formation |
| 1 | good film formation |

Wetting on Skin

| | |
|---|---|
| −1 | insufficient wetting on skin |
| 1 | sufficient wetting on skin |

Further, the spray shadow of the composition was evaluated. The numerical rating was as follows:

Spray Shadow

| | |
|---|---|
| −1 | insufficient spray shadow |
| 0 | decreased cone-shaped spray shadow |
| 1 | good cone-shaped spray shadow |

1.3 Viscosity Measurement

The viscosity of some of the samples was measured according to the determination by Ford cup. The principle of this viscosity determination is that the viscosity of the sample is measured as the amount of time required for the cup to empty by the liquid draining through the bottom orifice. Since viscosity is the resistance to flow, materials with a higher viscosity will take more time to drain through the hole in the cup. The measured time is given in the tables and may be converted to centistokes by multiplying the time to drain by a conversion factor provided for each cup size. The viscosity of the samples was measured at a temperature of 25° C. with Ford cup 3.

Example 2: Spray, Wetting and Sticking Properties on Skin of Aqueous Antimicrobial Film-Forming Teat Dip Compositions Diverse teat dip formulations were prepared and tested. First, compositions were formulated essentially according to the state of art described in document WO 98/04136, which comprise polyvinyl alcohol as film-forming element, polyvinylpyrrolidone iodine (PVP-iodine) and alkylbenzene sulfonic acid as active disinfectant substances, alkylether carboxylic acids as surfactant. After spraying the formulations onto the teats of cows using a Jetstream Gun (AJS/2402) having a fixed nozzle tip with O-ring (AJS2415) from Ambic® (Ambic Equipment Limited, UK), which is a vacuum operated sprayer. After spraying the quality of film formation, spray shadow and wetting on skin were evaluated. As shown in Table 1 the spray shadow, the film formation and/or the wetting on skin of the formulations according to the prior art were not sufficient for the intended use. Therefore, formulations F1 to F9 represent reference examples ("Ref. Ex.").

Further formulations were tested which in addition comprised a rheology modifier and tackifier in the form of xanthan gum (Rhodopol® G, Kelzan® T) and a mineral based rheology modifier (Optigel® CK). As shown in Table 2 the spray shadow of these formulations were not sufficient. Therefore, formulations A1 to A7 represent reference examples ("Ref. Ex.").

The tests on the formulations showed that when using currently available barrier products for spray application excessive foam formation was negatively influencing the barrier properties. However, low barrier properties in turn would lead to insufficient protection of the teat and the mammary ducts and therefore the formulations described in Tables 1 and 2 were unsuitable for the desired and intended spray application.

Then, formulations were tested which comprised a hydrophobically-modified ethoxylated urethane (HEUR) as rheology modifier and tackifier and/or an antifoaming agent. The HEURs evaluated included hydrophobically-modified ethoxylated urethanes having polyethylene glycol building blocks and urethane building blocks, and a polymer chain end-capped with hydrophobic groups. The hydrophobic groups included one or more of a $C_8$-$C_{40}$ linear alkyl, an aryl-substituted $C_2$-$C_{40}$ alkyl, a $C_2$-$C_{40}$ alkyl-substituted phenyl, a $C_8$-$C_{40}$ branched alkyl, a $C_8$-$C_{40}$ carbocyclic alkyl, or a $C_8$-$C_{80}$ complex ester. Surprisingly it was found that the spray shadow of these formulations were improved when using hydrophobically-modified ethoxylated urethane (HEUR) as rheology modifier and tackifier (F10, F11, F12, F14) and was further improved when combining this HEUR rheology modifier with an antifoaming agent (formulations F13, F15, F16, F18, F19, F20, F21 and F22).

The results summarized in tables 3 and 4 show that antimicrobial film-forming compositions comprising a hydrophobically-modified ethoxylated urethane (HEUR) as rheology modifier and tackifier according to the present invention have good spray, wetting and sticking properties on skin and which properties were further improved using in addition an antifoaming agent (formulations F13, F15, F16, F18, F19, F20, F21 and F22).

TABLE 1

Comparative examples using conventional ingredients (all amounts are given in wt.-%)

| Ingredient | Ref. Ex. F1 | Ref. Ex. F2 | Ref. Ex. F3 | Ref. Ex. F4 | Ref. Ex. F5 | Ref. Ex. F6 | Ref. Ex. F7 | Ref. Ex. F8 | Ref. Ex. F9 |
|---|---|---|---|---|---|---|---|---|---|
| polyvinyl alcohol | 2.5 | 2.5 | 2.5 | 2.5 | 2.5 | 3.0 | 3.5 | 2.5 | 2.5 |
| PVP-iodine | 1.35 | 1.35 | 1.35 | 1.35 | 1.35 | 1.35 | 1.35 | 1.35 | 1.35 |
| potassium iodate | 0.05 | 0.05 | 0.05 | 0.05 | 0.05 | 0.05 | 0.05 | 0.05 | 0.05 |
| glycerol (99.5%) | 5.0 | 5.0 | 5.0 | 5.0 | 5.0 | 5.0 | 5.0 | 5.0 | 5.0 |
| NaOH (50%) | 0.2661 | 0.5741 | 0.4201 | 0.2661 | 0.4201 | 0.2661 | 0.2661 | 0.3431 | 0.2969 |
| tartrazine E102 PAL | 0.051 | 0.051 | 0.051 | 0.051 | 0.051 | 0.051 | 0.051 | 0.051 | 0.051 |
| alkylether carboxylic acids | 0.798 | 1.862 | 1.33 | 0.798 | 1.33 | 0.798 | 0.798 | 1.064 | 0.9044 |
| alkylbenzene sulfonic acid | 0.201 | 0.469 | 0.335 | 0.201 | 0.335 | 0.201 | 0.201 | 0.268 | 02278 |
| polysulfonic acid | — | — | — | 0.5 | 0.5 | — | — | — | — |
| distilled water | ad 100 wt.-% | | | | | | | | |
| film formation | −1 | 1 | 1 | 1 | 1 | 1 | 1 | 1 | 1 |
| spray shadow | 1 | −1 | −1 | −1 | −1 | −1 | −1 | −1 | −1 |
| wetting on skin | −1 | 1 | 1 | 1 | 1 | 1 | 1 | 1 | 1 |

TABLE 2

Comparative examples using diverse rheology modifiers (all amounts are given in wt.-%)

| ingredient | Ref. Ex. A1 | Ref. Ex. A2 | Ref. Ex. A3 | Ref. Ex. A4 | Ref. Ex. A5 | Ref. Ex. A6 | Ref. Ex. A7 |
|---|---|---|---|---|---|---|---|
| polyvinyl alcohol | 2.5 | 2.5 | 2.5 | 5.0 | 5.0 | 5.0 | 2.5 |
| PVP-iodine | 1.35 | 1.35 | 1.35 | 1.35 | 1.35 | 1.35 | 1.35 |
| potassium iodate | 0.05 | 0.05 | 0.05 | 0.05 | 0.05 | 0.05 | 0.05 |
| glycerol (99.5%) | 5.0 | 5.0 | 5.0 | 5.0 | 5.0 | 5.0 | 5.0 |
| NaOH (50%) | 0.2661 | 0.2661 | 0.2661 | 0.2661 | 0.2661 | 0.2661 | 0.2661 |
| tartrazine E102 PAL | 0.051 | 0.051 | 0.051 | 0.051 | 0.051 | 0.051 | 0.051 |
| alkylether carboxylic acids | 0.798 | 0.798 | 0.798 | 0.798 | 0.798 | 0.798 | 0.798 |
| alkylbenzene sulfonic acid | 0.201 | 0.201 | 0.201 | 0.201 | 0.201 | 0.201 | 0.201 |
| Rhodopol ® G (Xanthan gum) | 0.48 | — | — | 0.48 | — | — | — |
| Kelzan ® T (Xanthan gum) | — | 0.48 | 0.2 | — | 0.48 | 0.2 | — |
| Optigel ® CK (mineral based rheology modifier) | — | — | — | — | — | — | 3.0 |
| HEUR | — | — | — | — | — | — | — |
| antifoam | — | — | — | — | — | — | — |
| distilled water | | | | ad 100 wt.-% | | | |
| pH value | 4.6 | 4.6 | 4.5 | 4.5 | 4.6 | 4.7 | 4.7 |
| viscosity (Ford cup 3) | n.d. | n.d. | n.d. | n.d. | n.d. | n.d. | n.d. |
| film formation | 1 | 1 | 1 | 1 | 1 | 1 | 1 |
| spray shadow | −1 | −1 | −1 | −1 | −1 | −1 | −1 |
| wetting on skin | 1 | 1 | 1 | 1 | 1 | 1 | 1 |

TABLE 3

Examples according to the invention using HEUR as rheology modifier (all amounts are given in wt.-%)

| Ingredient | Ex. F10 | Ex. F11 | Ex. F12 | Ex. F13 | Ex. F14 | Ex. F15 | Ex. F16 |
|---|---|---|---|---|---|---|---|
| polyvinyl alcohol | 2.5 | 2.5 | 2.5 | 2.5 | 2.5 | 2.5 | 3.0 |
| PVP-iodine | 1.35 | 1.35 | 1.35 | 1.35 | 1.35 | 1.35 | 1.35 |
| potassium iodate | 0.05 | 0.05 | 0.05 | 0.05 | 0.05 | 0.05 | 0.05 |
| glycerol (99.5%) | 5.0 | 5.0 | 5.0 | 5.0 | 5.0 | 5.0 | 5.0 |
| NaOH (50%) | 0.2661 | 0.2661 | 0.2661 | 0.2661 | 0.2661 | 0.2661 | 0.2661 |
| tartrazine E102 PAL | 0.051 | 0.051 | 0.051 | 0.051 | 0.051 | 0.051 | 0.051 |
| alkylether carboxylic acids | 0.798 | 0.798 | 0.798 | 0.798 | 0.798 | 0.798 | 0.798 |
| alkylbenzene sulfonic acid | 0.201 | 0.201 | 0.201 | 0.201 | 0.201 | 0.201 | 0.201 |
| HEUR | 0.5 | 1.0 | 0.5 | 0.5 | 1.0 | 1.0 | 0.5 |
| antifoam | — | — | — | 0.05 | — | 0.05 | 0.05 |
| distilled water | | | | ad 100 wt.-% | | | |
| pH value | 4.1 | 5.3 | 5.3 | 5.1 | 5.5 | 5.0 | 5.2 |
| viscosity (Ford cup 3) | 23 sec. | 24 sec. | 23 sec. | 22 sec. | 24 sec. | 24 sec. | 23 sec. |
| film formation | 1 | 1 | 1 | 1 | 1 | 1 | 1 |
| spray shadow | 1 | 1 | 1 | 1+ | 1 | 1+ | 1++ |
| wetting on skin | 1 | 1 | 1 | 1 | 1 | 1 | 1 |

TABLE 4

Examples according to the invention using HEUR as rheology modifier and reference example (all amounts are given in wt.-%)

| Ingredient | Ref. Ex. F17 | Ex. F18 | Ex. F19 | Ex. F20 | Ex. F21 | Ex. F22 |
|---|---|---|---|---|---|---|
| polyvinyl alcohol | 3.5 | 3.0 | 3.0 | 3.0 | 3.0 | 2.5 |
| PVP-iodine | 1.35 | 1.35 | 1.35 | 1.35 | 1.35 | 1.35 |
| potassium iodate | 0.05 | 0.05 | 0.05 | 0.05 | 0.05 | 0.05 |
| glycerol (99.5%) | 5.0 | 5.0 | 5.0 | 5.0 | 5.0 | 5.0 |
| NaOH (50%) | 0.2661 | 0.2661 | 0.2661 | 0.2661 | 0.2661 | 0.2661 |
| tartrazine E102 PAL | 0.051 | 0.051 | 0.3 | 0.051 | 0.051 | 0.3 |
| alkylether carboxylic acids | 0.798 | 0.798 | 0.798 | 0.798 | 0.798 | 0.798 |
| alkylbenzene sulfonic acid | 0.201 | 0.201 | 0.201 | 0.45 | 0.45 | 0.201 |
| HEUR | — | 0.25 | 0.5 | 1.5 | 0.5 | 0.5 |
| antifoam | 0.05 | 0.05 | 0.05 | 0.05 | 0.05 | 0.05 |
| distilled water | | | ad 100 wt.-% | | | |
| pH value | 5.0 | 5.3 | 5.1 | 5.2 | 5.4 | 5.3 |

TABLE 4-continued

Examples according to the invention using HEUR as rheology modifier and reference example (all amounts are given in wt.-%)

| Ingredient | Ref. Ex. F17 | Ex. F18 | Ex. F19 | Ex. F20 | Ex. F21 | Ex. F22 |
|---|---|---|---|---|---|---|
| viscosity (Ford cup 3) | n.a. | 19 sec. | 25 sec. | 23 sec. | 22 sec. | 18 sec. |
| film formation | 1 | 1 | 1 | 1 | 1 | 1 |
| spray shadow | −1 | 1 | 1+++ | 1+++ | 1+++ | 1+++ |
| wetting on skin | 1 | 1 | 1 | 1 | 1 | 1 |

Example 3: The Influence of Storage on the Spray Nozzle

Further, the formulations of the present invention were also tested towards their characteristics in spray guns and spray nozzles over a prolonged time period. Therefore, the formulations were tested in respect to the quality of their spray shadow after one week storage of a Jetstream Gun (AJS/2402) having a fixed nozzle tip with O-ring (AJS2415) from Ambic® (Ambic Equipment Limited, UK), which is a vacuum operated sprayer at ambient (20° C.) temperature. The criteria relating to the quality of film formation, spray shadow and wetting on skin were evaluated. The observed result was that the formulations according to the present invention (F10-F16, F18-F22) showed good film building properties, a good cone-shaped spray shadow and sufficient wetting on skin, when freshly prepared as well as when spraying after one week storage in the Jetstream Gun. Further, no nozzle failure was observed after one week storage in the Jetstream Gun, when using the formulation according to the present invention (formulations F13, F19, F22).

Example 4: The Influence of the Temperature

As an example, formulation F22 was tested in respect to its properties at different temperatures in respect to viscosity and freezing point. The viscosity of the samples was measured according to the determination by Ford cup using cup 3. The viscosity of the samples was measured at temperatures in the range from 20° C. to −8° C. The viscosity is reflected by the amount of time required for the cup to empty by the liquid draining through the bottom orifice of the cup. The results are shown in Table 5.

TABLE 5

The influence of the temperature on the formulation

| | temperature | | | | | | |
|---|---|---|---|---|---|---|---|
| | 20° C. | 10° C. | 7° C. | 4° C. | 0° C. | −5° C. | −8° C. |
| viscosity | 23 sec. | 24 sec. | 26 sec. | 26 sec. | 26 sec. | 27 sec. | freezing point |

The invention claimed is:

1. A sprayable aqueous antimicrobial film-forming composition for teats comprising in an aqueous base:
   (a) from 1.0 wt.-% to 5.0 wt.-% of a first film-forming polymer, wherein the first film-forming polymer is a polyvinyl alcohol;
   (b) from 0.05 wt.-% to 5.0 wt.-% of a second film-forming polymer, wherein the second film-forming polymer is a polysulfonic acid;
   (c) from 0.1 wt.-% to 10.0 wt.-% of an antimicrobial agent, wherein the antimicrobial agent is polyvinylpyrrolidone iodine (PVP-iodine);
   (d) from 0.001 wt.-% to 3.0 wt.-% of a hydrophobically-modified ethoxylated urethane rheology modifier having polyethylene glycol building blocks and urethane building blocks, and a polymer chain end-capped with hydrophobic groups; wherein the hydrophobic groups comprise a $C_8$-$C_{40}$ linear alkyl, an aryl-substituted $C_2$-$C_{40}$ alkyl, a $C_2$-$C_{40}$ alkyl-substituted phenyl, a $C_8$-$C_{40}$ branched alkyl, a $C_8$-$C_{40}$ carbocyclic alkyl, a $C_8$-$C_{80}$ complex ester, or a combination thereof;
   (e) from 0.005 wt.-% to 1.0 wt.-% of an anti-foaming agent comprising a hydrophobic silica and/or silicone;
   (f) from 0.05 wt.-% to 4.0 wt.-% of an alkyl ether carboxylic acid having the formula:

$$R-O-(C_3H_6-O)_m-(C_2H_4-O)_n-CH_2-COOH,$$

wherein R is an alkyl group having 4 to 10 carbon atoms, m is an integer from 0 to 8, and n is an integer from 0 to 8, and wherein at least one of m or n is not 0; and/or $$R-O-(C_2H_4-O)_n-CH_2-COOH,$$

wherein R is an alkyl group having 4 to 10 carbon atoms, and n is an integer from 2 to 8; and
   (g) optionally from 0.01 wt.-% to 5.0 wt.-% of an additional antimicrobial agent comprising an alkylbenzene sulfonic acid, chlorhexidine, orthophenyl phenol, lactic acid, decanoic acid, or a combination thereof.

2. The sprayable aqueous antimicrobial film-forming composition of claim 1, wherein the composition comprises from 0.5 wt.-% to 10.0 wt.-% of the antimicrobial agent.

3. The sprayable aqueous antimicrobial film-forming composition of claim 1, wherein the composition comprises from 0.5 wt.-% to 7.0 wt.-% of the antimicrobial agent.

4. The sprayable aqueous antimicrobial film-forming composition of claim 1, wherein the composition comprises from 2.0 wt.-% to 4.5 wt.-% of the first film-forming polymer, from 0.5 wt.-% to 5.0 wt.-% of the antimicrobial agent, from 0.05 wt.-% to 0.5 wt.-% of the rheology modifier, and from 0.02 wt.-% to 0.2 wt.-% of the anti-foaming agent.

5. The sprayable aqueous antimicrobial film-forming composition of claim 1, wherein the composition reduces the incidence of both contagious mastitis and environmental mastitis in a dairy herd.

6. The sprayable aqueous antimicrobial film-forming composition of claim 1, wherein the additional antimicrobial agent is an alkylbenzene sulfonic acid.

7. The sprayable aqueous antimicrobial film-forming composition of claim 1, wherein the composition has a Brookfield viscosity of from 1 cPs to 50 cPs at a temperature of 25° C. when measured using a spindle #2 at 50 rpm.

8. A sprayable aqueous antimicrobial composition for teats comprising in an aqueous base:
   (a) from 1.0 wt.-% to 5.0 wt. % of a first film-forming polymer, wherein the first film-forming polymer is a polyvinyl alcohol having a polymethylene backbone;
   (b) from 0.05 wt-% to 5.0 wt-% of a second film-forming polymer, wherein the second film forming polymer is a polysulfonic acid;
   (c) from 0.1 wt.-% to 10.0 wt.-% of an antimicrobial agent, wherein the antimicrobial agent is polyvinylpyrrolidone iodine (PVP-iodine);
   (d) from 0.001 wt.-% to 3.0 wt.-% of a hydrophobically-modified ethoxylated urethane rheology modifier having polyethylene glycol building blocks and urethane building blocks, and a polymer chain end-capped with hydrophobic groups, as a rheology modifier;
   (d) from 0.05 wt-% to 4.0 wt-% of an alkyl ether carboxylic acid having the formula:

R—O—(C$_3$H$_6$—O)$_m$—(C$_2$H$_4$—O)$_n$—CH$_2$—COOH, wherein R is an alkyl group having 4 to 10 carbon atoms, m is an integer from 0 to 8, and n is an integer from 0 to 8, and wherein at least one of m or n is not 0; and/or R—O—(C$_2$H$_4$—O)$_n$—CH$_2$—COOH, wherein R is an alkyl group having 4 to 10 carbon atoms, and n is an integer from 2 to 8;
   (f) from 0.005 wt-% to 1.0 wt.-% of an anti-foaming agent, wherein the anti-foaming agent is a hydrophobic silica and/or silicone; and
   (g) from 0.01 wt-% to 5.0 wt-% of an additional antimicrobial agent comprising an alkylbenzene sulfonic acid, chlorhexidine, orthophenyl phenol, lactic acid, decanoic acid, or a combination thereof.

9. A method for controlling mastitis in milk producing animals comprising:
   providing the composition according to claim 1, and
   applying the composition to the surface of a teat.

10. The method of claim 9, wherein the composition is applied by spraying the composition on a teat.

* * * * *

UNITED STATES PATENT AND TRADEMARK OFFICE
CERTIFICATE OF CORRECTION

PATENT NO. : 11,116,215 B2
APPLICATION NO. : 15/739087
DATED : September 14, 2021
INVENTOR(S) : Tillmann Kleine et al.

It is certified that error appears in the above-identified patent and that said Letters Patent is hereby corrected as shown below:

In the Claims

Column 29, Claim 8, Line 3:
DELETE "5.0 wt. %" after "to"
INSERT --5.0 wt.-%-- after "to"

Column 29, Claim 8, Line 6:
DELETE "0.05 wt-% to 5.0 wt-%" after "from"
INSERT --0.05 wt.-% to 5.0 wt.-%-- after "from"

Column 29, Claim 8, Line 17:
DELETE "groups, as a rheology modifier;" after "hydrophobic"
INSERT --groups;-- after "hydrophobic"

Column 29, Claim 8, Line 18:
DELETE "(d)" before "from"
INSERT --(e)-- before "from"

Column 29, Claim 8, Line 18:
DELETE "0.05 wt-% to 4.0 wt-%" after "from"
INSERT --0.05 wt.-% to 4.0 wt.-%-- after "from"

Column 30, Claim 8, Line 8:
DELETE "0.005 wt-%" after "from"
INSERT --0.005 wt.-%-- after "from"

Column 30, Claim 8, Line 11:
DELETE "0.01 wt-% to 5.0 wt-%" after "from"
INSERT --0.01 wt.-% to 5.0 wt.-%-- after "from"

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,116,215 B2

<u>Column 30, Claim 9, Line 17:</u>
DELETE "claim 1," after "to"
INSERT --claim 1;-- after "to"